(12) United States Patent
Biesel

(10) Patent No.: US 8,858,493 B2
(45) Date of Patent: Oct. 14, 2014

(54) CAP, PARTICULARLY A DISINFECTION CAP, DETECTION DEVICE FOR PERITONEAL DIALYSIS, BAG SET FOR PERITONEAL DIALYSIS, AND THE USE THEREOF

(75) Inventor: Wolfgang Biesel, Ottweiler (DE)

(73) Assignee: Fresenius Medical Care Deutschland GmbH, St. Wendel (DE)

( * ) Notice: Subject to any disclaimer, the term of this patent is extended or adjusted under 35 U.S.C. 154(b) by 1463 days.

(21) Appl. No.: 11/628,371

(22) PCT Filed: Jun. 3, 2005

(86) PCT No.: PCT/DE2005/001002
§ 371 (c)(1),
(2), (4) Date: Dec. 1, 2006

(87) PCT Pub. No.: WO2005/120604
PCT Pub. Date: Dec. 22, 2005

(65) Prior Publication Data
US 2008/0015492 A1    Jan. 17, 2008

(30) Foreign Application Priority Data
Jun. 7, 2004  (DE) .......................... 10 2004 027 743

(51) Int. Cl.
*A61M 1/00*  (2006.01)
*A61M 1/28*  (2006.01)

(52) U.S. Cl.
CPC ....... *A61M 1/285* (2013.01); *A61M 2205/6063* (2013.01); *A61M 2205/6081* (2013.01); *A61M 1/287* (2013.01); *A61M 2205/582* (2013.01); *A61M 2205/18* (2013.01); *A61M 2205/6072* (2013.01); *A61M 1/28* (2013.01)
USPC .............. 604/29; 604/535; 604/256; 604/408

(58) Field of Classification Search
CPC ....... A61M 1/28; A61M 1/285; A61M 1/287; A61M 2205/18; A61M 2205/582; A61M 2205/6063; A61M 2205/6072; A61M 2205/6081
USPC ......... 604/29, 408, 535, 256, 533; 206/459.1, 206/459.5; 422/28
See application file for complete search history.

(56) References Cited

U.S. PATENT DOCUMENTS 4,403,992 A  9/1983 Bertellini et al.
4,440,207 A  4/1984 Genatempo et al.
(Continued)

FOREIGN PATENT DOCUMENTS

DE  198 14 047 C1  3/1998
DE  100 42 067 A1  3/2002
(Continued)

*Primary Examiner* — Kami A Bosworth
*Assistant Examiner* — Imani Hayman
(74) *Attorney, Agent, or Firm* — Collard & Roe, P.C.

(57) ABSTRACT

A cap, especially a disinfectant cap, is for protecting and/or closing off the abdominal connector used in peritoneal dialysis, and to a detection device for peritoneal dialysis. There is a bag set for peritoneal dialysis and use thereof. In view of the sometimes serious consequences of an incorrect sequence of fluids in the patient's abdominal cavity, it is desirable to prevent an incorrect sequence of fluids during peritoneal dialysis. This is achieved by providing the cap, especially a disinfectant cap, with information about the medium contained at any one time in the patient's abdominal cavity. In this way it is always possible—even after the fluid has been dispensed into the abdominal cavity and the bag disposed of—to determine which medium is currently in the patient's abdominal cavity and/or to record other details, such as the amount, the concentration, the manufacturer, etc. of the medium, and to take this information into account, especially during subsequent stages of the peritoneal dialysis treatment.

25 Claims, 3 Drawing Sheets

(56) References Cited

U.S. PATENT DOCUMENTS

Figure 1:
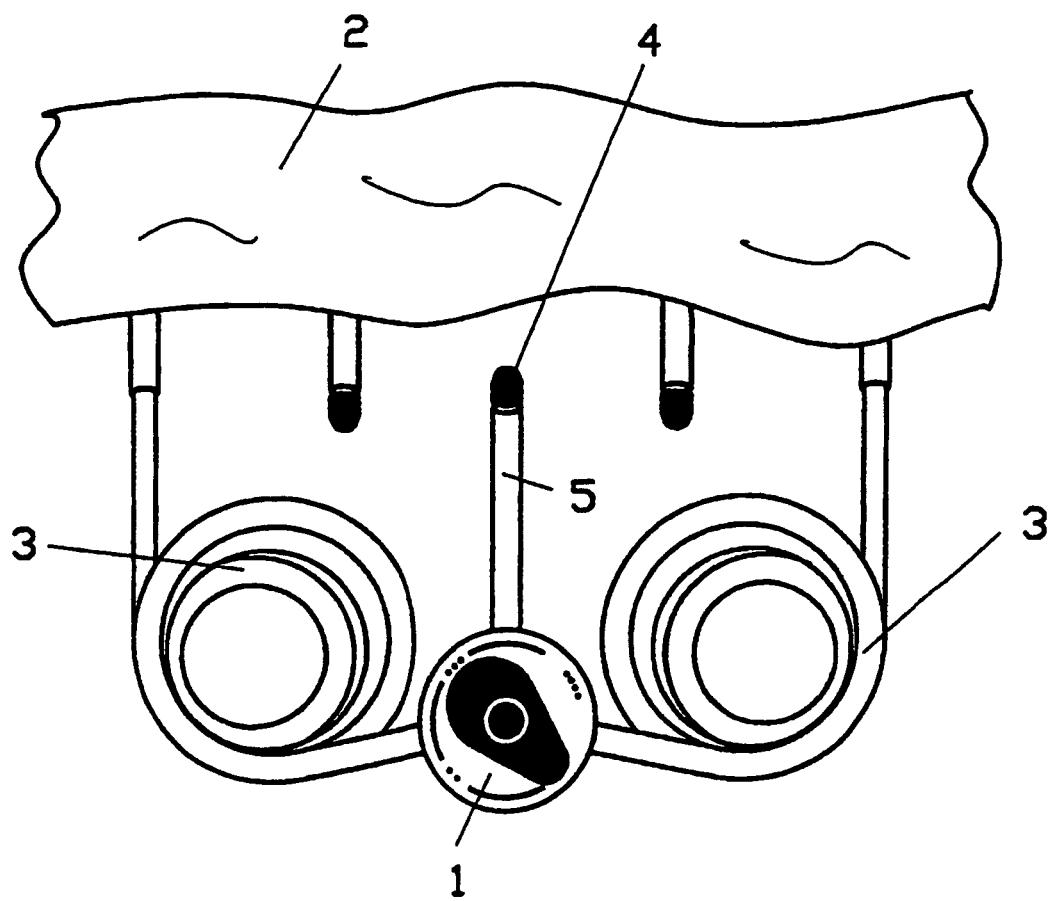

| | | | |
|---|---|---|---|
| 4,983,161 A * | 1/1991 | Dadson et al. | 604/28 |
| 5,011,032 A * | 4/1991 | Rollman | 215/230 |
| 5,377,853 A * | 1/1995 | Papciak | 215/230 |
| 5,713,850 A | 2/1998 | Heilmann et al. | |
| 6,196,992 B1 * | 3/2001 | Keilman et al. | 604/67 |
| 6,482,189 B2 | 11/2002 | Döpper et al. | |
| 2003/0153865 A1 * | 8/2003 | Connell et al. | 604/28 |

FOREIGN PATENT DOCUMENTS

| | | |
|---|---|---|
| EP | 0 715 860 B1 | 12/1995 |
| WO | WO 86/02907 | 5/1986 |
| WO | WO 94/28855 | 12/1994 |

* cited by examiner

CAP, PARTICULARLY A DISINFECTION CAP, DETECTION DEVICE FOR PERITONEAL DIALYSIS, BAG SET FOR PERITONEAL DIALYSIS, AND THE USE THEREOF

CROSS REFERENCE TO RELATED APPLICATIONS

Applicant claims priority under 35 U.S.C. §119 of German Application No. 10 2004 027 743.4 filed Jun. 7, 2004. Applicant also claims priority under 35 U.S.C. §365 of PCT/DE2005/001002 filed Jun. 3, 2005. The international application under PCT article 21(2) was not published in English.

The invention relates to a cap, especially a disinfectant cap, for protecting and /or closing off the abdominal connector used in peritoneal dialysis, and to a detection device for peritoneal dialysis. The invention relates further to a bag set for peritoneal dialysis and use thereof.

Patient connectors for peritoneal dialysis are known, for example from EP 0 715 860 B1 or DE 198 14 047 C1. These permit sterile connection and disconnection of patients undergoing peritoneal dialysis treatment. With patient connectors of this kind, a closure plug is inserted on completion of peritoneal dialysis into the connector of the tube portion leading to the patient's abdominal cavity. In addition, it is usual to fit a sterile disinfectant cap onto the abdominal connector in order to prevent germs from getting into the connector. The access to the patient's abdominal cavity is thus closed off in sterile manner.

Although it is normally indicated on the containers—which are routinely configured as bags—which liquid they contain and how much, this information is no longer available once the liquid has been dispensed and the bag disposed of. Since, for example in the case of CAPD (continuous ambulatory peritoneal dialysis), solutions with different glucose concentrations, osmotic components or nutrients have to be used by the patient in a given sequence over a given period of time, it can easily happen that the patient no longer remembers which fluid is currently contained in his/her abdominal cavity, and how much. The problem is exacerbated in cases where the patient becomes unconscious and can no longer provide any information as to the last solution used, or in cases of hospital treatment where the end of a shift means a staff change-over and there may be gaps in the log book.

In view of the sometimes serious consequences of an incorrect sequence of fluids in the patient's abdominal cavity, the object of this invention is to prevent an incorrect sequence of fluids during peritoneal dialysis.

This object is established according to the invention by providing the cap, especially a disinfectant cap, with information about the medium contained at any one time in the patient's abdominal cavity.

In this way it is always possible—even after the fluid has been dispensed into the abdominal cavity and the bag disposed of—to determine which medium is currently in the patient's abdominal cavity and/or to record other details, such as the amount, the concentration, the manufacturer, etc. of the medium, and to take this information into account, especially during subsequent stages of the peritoneal dialysis treatment.

It is within the scope of the invention that the information relates to the nature of the medium. This information can serve to identify each of the solutions used, e.g., to differentiate between a glucose-containing and an amino-acid-containing solution.

It is likewise within the scope of the invention that the information relates to the amount of medium.

It is additionally useful that the information relates to the concentration of the medium.

Since solutions having different concentrations of a medium are used in peritoneal dialysis, e.g. calcium solutions with 1.0%, 1.25% or 1.75% calcium, it makes sense to include also the concentration in the coding.

According to the invention, the information is provided on the cap in the form of a colour code, a bar code, symbols, or in tactile form, especially Braille.

These are just some examples—the list can be extended arbitrarily—of how the information can be provided on the cap.

It is to advantage if the cap and the bag system to which it belongs form a unit.

This measure ensures that the cap characteristic of a particular bag system is delivered along with that bag system, so that, firstly, use is always made of a new, sterile cap, and, secondly, the bag system is visibly identified by the cap provided with the information.

A useful development of the invention consists in that a closure plug, which is separate from the cap and serves to close off the abdominal connector, is also provided with the same information as the particular cap.

Since it is possible either to use a cap that also serves as closure cap for the abdominal connector, i.e. a cap that closes off the abdominal connector and simultaneously protects against germs, or to separate these two functions, i.e. to use a closure plug and a cap, it makes sense in the latter case to mark both components in accordance with the last-dispensed solution.

The scope of the invention also includes a detection device for peritoneal dialysis, the detection device having means to process information provided on a cap, especially a disinfectant cap, about the medium contained at any one time in the patient's abdominal cavity.

A detection device of this kind can interact advantageously with the cap and prevent an incorrect sequence of fluids during peritoneal dialysis.

The invention also provides for the provision of means to output the information.

The detection device can thus serve to output the information, be it via text or voice display, so that besides the user, also third persons (e.g. the nursing staff in a hospital) can obtain information about the fluid currently in use.

A useful development of the invention consists in that the detection device has means to trigger an alarm on connection of an incorrect medium.

If the sequence of fluids to be used, or at least any incompatibilities between successive solutions, are stored in the detection device, it can trigger an alarm in such a case and warn against an incorrect sequence.

The invention relates further to a bag set for peritoneal dialysis, the set comprising at least one bag with fluid and a cap, in particular a disinfectant cap, and the cap bearing information about the content of the bag, in particular about the nature, amount and concentration of the content.

This makes it possible to distinguish between two such bag sets by way of the information provided on the cap.

The cap can be designed to remain on the patient's abdominal connector.

It is within the scope of the invention that the information is provided on the cap in the form of a colour code, a bar code, symbols or in tactile form, especially Braille.

The invention relates lastly to the use of a bag set for peritoneal dialysis, said bag set containing at least one bag with fluid and a cap, especially a disinfectant cap, with the cap bearing information about the content of the bag, in particular about the nature, amount and concentration of the content, and remaining on the patient's abdominal connector after the fluid has been dispensed into his/her abdominal cavity.

The advantages of the invention consist in that not only the user but also third parties can obtain, maybe by way of a detection device, the information relevant to the particular solution in use during peritoneal dialysis, and that, in addition, a warning can be triggered automatically in the case of an incorrect sequence of solutions.

Figure 2:
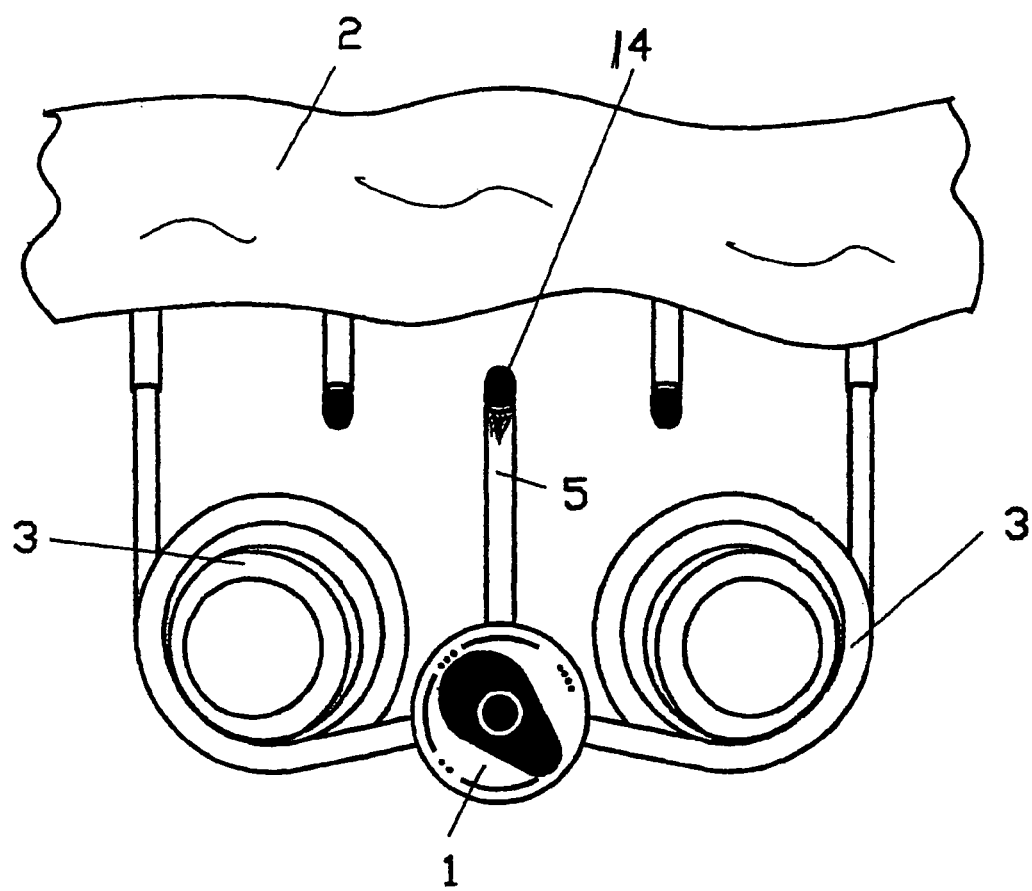
Figure 3:
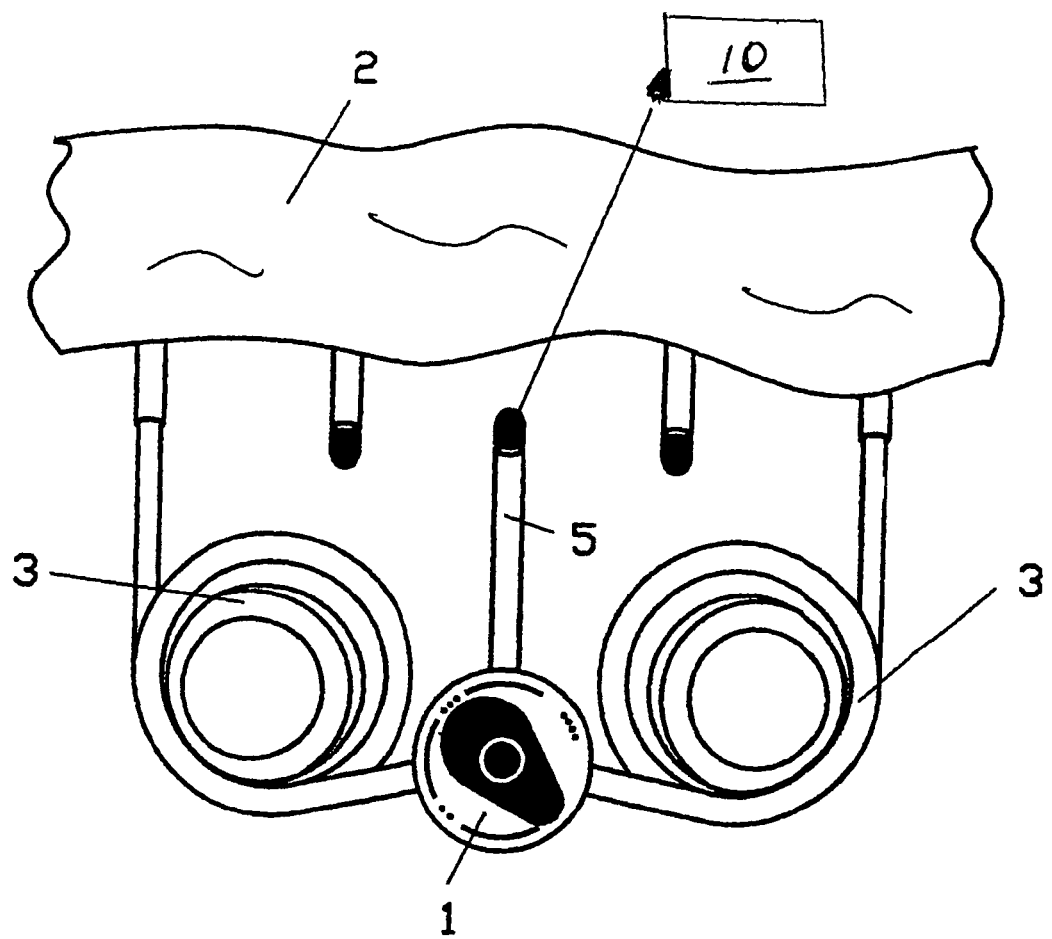

In the following, several embodiments of the invention are explained by reference to the drawings, in which:

FIG. 1 shows a patient connector with a cap according to the invention; FIG. 2 shows a patient connector with a closure plug according to the invention; and FIG. 3 shows a patient connector with a detection device according to the invention.

As is evident from FIG. 1, a patient connector 1 is connected via hoses 3 to a bag system 2 for peritoneal dialysis. The patient connector 1 has a cap 4, especially a disinfectant cap 4, which is connected to the patient connector 1 via an intermediate member 5. The intermediate member 5 is divided in the middle and keeps both the cap 4 and the patient connector 1 in sterile condition. To change the solutions, the patient connector 1 is connected to the patient's abdominal connector. Subsequently, the abdominal connector is closed off again by means of a closure plug 14 (in FIG. 2) and the cap 4, or by means of a cap 4 that also performs a closing function.

To prevent mix-ups and permit retrieval of the information pertaining to the solution in use at any one time, a cap 4 is used that carries this information, for example in the form of a colour code, a bar code, symbols or a tactile code (e.g. in Braille). This information can be read with an appropriate detection device 10 (in FIG. 3) provided with a colour recognition system, a bar-code reader or an optical sensor.

An example of coding of this nature is given in the table below:

| Substance/concentration | Colour | Tactile bump |
|---|---|---|
| 1.5% glucose | Yellow | 1 |
| 2.3% glucose | Green | 2 |
| 4.25% glucose | Red | 3 |
| Amino acid | Blue | 4 |
| Polyglucose | Violet | 5 |
| 1.0% calcium ($Ca^{++}$) | 0-33% black | None |
| 1.25% calcium ($Ca^{++}$) | 34-66% black | None |
| 1.75% calcium ($Ca^{++}$) | 67-100% black | None |

An appropriate coding can naturally be provided for other substances used in dialysis solutions. It is also possible to provide coding combinations, e.g. for a certain glucose concentration and a certain calcium concentration.

After filling of the peritoneum, the cap 4 remains on the patient's abdominal connector so that the liquid contained in the peritoneum can be read off at the disinfectant cap 4 used in each case.

This measure makes it possible to call up the information even if a patient has become unconscious, or to obtain a warning in the case of an incorrect sequence of solutions.

The invention claimed is:

1. A coded disinfectant cap (4), for protecting and/or closing off a patient's abdominal connector used in peritoneal dialysis, wherein a bag set for peritoneal dialysis contains at least one bag (2) with a fluid and the coded disinfectant cap (4), the coded disinfectant cap (4) providing information on contents of the bag, the coded disinfectant cap (4) is used for closing the patient's abdominal connector and is provided with information about a medium contained at any one time in a patient's abdominal cavity, and the information being detectable during use of the bag set for peritoneal dialysis; and wherein the coded disinfectant cap (4) is suitable for closing off the patient's abdominal connector and protecting it from germs; and wherein the information is provided on the coded disinfectant cap (4) in the form of a color code, a bar code, symbols, or in tactile form.

2. The coded disinfectant cap (4) of claim 1, wherein the information relates to a nature of the medium.

3. The coded disinfectant cap (4) of claim 1, wherein the information relates to an amount of the medium.

4. The coded disinfectant cap (4) of claim 1, wherein the information relates to a concentration of the medium.

5. The coded disinfectant cap (4) of claim 1, wherein the coded disinfectant cap (4) and a bag (2) to which it belongs form a unit.

6. The coded disinfectant cap (4) of claim 1, wherein a closure plug, which is separate from the coded disinfectant cap (4) and serves to close off the patient's abdominal connector, is also provided with the same information as the coded disinfectant cap(4).

7. The coded disinfectant cap of claim 1, wherein the information triggers a warning automatically in the case of an incorrect sequence of solutions.

8. The coded disinfectant cap of claim 1, wherein the information provides coding combinations.

9. The coded disinfectant cap of claim 8, wherein the coding combinations are for a certain glucose concentration and a certain calcium concentration.

10. A bag set for peritoneal dialysis, wherein the bag set contains at least one bag (2) with fluid and a coded disinfectant cap (4), the coded disinfectant cap (4) bearing information about contents of the bag, in particular about a nature, an amount and a concentration of the contents, and the coded disinfectant cap (4) is used for closing an abdominal connector of the patient so that the coded disinfectant cap (4) is designed to remain on the patient's abdominal connector; and the information being detectable during use of the bag set for peritoneal dialysis; and, wherein the coded disinfectant cap (4) is suitable for closing off the patient's abdominal connector and protecting it from germs; and wherein the information is provided on the coded disinfectant cap (4) in the form of a color code, a bar code, symbols, or in tactile form.

11. The bag set of claim 10, wherein the information triggers a warning automatically in the case of an incorrect sequence of solutions.

12. The bag set of claim 10, wherein the information provides coding combinations.

13. The bag set of claim 12, wherein the coding combinations are for a certain glucose concentration and a certain calcium concentration.

14. A bag set for peritoneal dialysis, said bag set containing at least one bag (2) with fluid and a coded disinfectant cap (4), with the coded disinfectant cap (4) bearing information about contents of the bag (2), in particular about a nature, an amount and a concentration of the contents, and the coded disinfectant cap (4) remains on a patient's abdominal connector after the fluid has been dispensed into his/her abdominal cavity; and the information being detectable during use of the bag set for peritoneal dialysis; and wherein the coded disinfectant cap (4) is suitable for closing off the patient's abdominal connector and protecting it from germs.

15. The bag set of claim 14, wherein the information triggers a warning automatically in the case of an incorrect sequence of solutions.

16. The bag set of claim 14, wherein the information provides coding combinations.

17. The bag set of claim 16, wherein the coding combinations are for a certain glucose concentration and a certain calcium concentration.

18. A bag system for peritoneal dialysis, comprising at least one bag (2) for holding a medium and a coded disinfectant cap (4) for protecting and/or closing off an abdominal connector used in peritoneal dialysis, wherein the coded disinfectant cap is provided with information on the medium in form of a color code, a bar code, symbols, or a tactile form, and wherein the bag system contains the coded disinfectant cap (4); and
   the information being detectable during use of the bag set for peritoneal dialysis; and wherein the coded disinfectant cap (4) is suitable for closing off the patient's abdominal connector and protecting it from germs.

19. The bag system of claim 18, wherein a closure plug, which is separate from the coded disinfectant cap (4) and serves to close off the abdominal connector, is also provided with the same information as the coded disinfectant cap (4).

20. The bag system of claim 18, wherein the coded disinfectant cap (4) is designed to remain on the patient's abdominal connector.

21. The bag system of claim 18, wherein the cap (4) is a disinfectant cap.

22. The bag system of claim 18, wherein the tactile form is Braille.

23. The bag system of claim 18, wherein the information triggers a warning automatically in the case of an incorrect sequence of solutions.

24. The bag system of claim 18, wherein the information provides coding combinations.

25. The bag system of claim 24, wherein the coding combinations are for a certain glucose concentration and a certain calcium concentration.

* * * * *